(12) United States Patent
Ootake et al.

(10) Patent No.: US 9,987,201 B2
(45) Date of Patent: Jun. 5, 2018

(54) OIL-IN-WATER TYPE EMULSIFIED COSMETIC

(71) Applicant: SHISEIDO COMPANY, LTD., Tokyo (JP)

(72) Inventors: Sawako Ootake, Yokohama (JP); Hideki Shimizu, Yokohama (JP)

(73) Assignee: SHISEIDO COMPANY, LTD., Tokyo (JP)

(*) Notice: Subject to any disclaimer, the term of this patent is extended or adjusted under 35 U.S.C. 154(b) by 0 days. days.

(21) Appl. No.: 15/116,950

(22) PCT Filed: Mar. 17, 2015

(86) PCT No.: PCT/JP2015/057832
§ 371 (c)(1),
(2) Date: Aug. 5, 2016

(87) PCT Pub. No.: WO2015/146702
PCT Pub. Date: Oct. 1, 2015

(65) Prior Publication Data
US 2017/0172858 A1 Jun. 22, 2017

(30) Foreign Application Priority Data
Mar. 26, 2014 (JP) .................................. 2014-062961

(51) Int. Cl.
*A61K 8/06* (2006.01)
*A61K 8/29* (2006.01)
*A61K 8/60* (2006.01)

(52) U.S. Cl.
CPC ................ *A61K 8/062* (2013.01); *A61K 8/29* (2013.01); *A61K 8/60* (2013.01)

(58) Field of Classification Search
None
See application file for complete search history.

(56) References Cited

U.S. PATENT DOCUMENTS

2010/0135938 A1   6/2016   Ishikubo et al.

FOREIGN PATENT DOCUMENTS

| JP | H8-104613 | 4/1996 |
|---|---|---|
| JP | 09-221411 | 8/1997 |
| JP | H11-504043 | 4/1999 |
| JP | 11-158036 | 6/1999 |
| JP | 2000 072623 | 3/2000 |
| JP | 2001-518939 | 10/2001 |
| JP | 2002-154927 | 5/2002 |
| JP | 2004-323473 | 11/2004 |
| JP | 2005-225827 | 8/2005 |
| JP | 2005-527595 | 9/2005 |
| JP | 2007-277191 | 10/2007 |
| JP | 2008-56535 | 3/2008 |
| JP | 2009-149555 | 7/2009 |
| JP | 2011-72310 | 4/2011 |
| JP | 2012 001500 | 1/2012 |
| JP | 2012-62265 | 3/2012 |
| JP | 2012-87084 | 5/2012 |
| JP | 2012-111726 | 6/2012 |
| JP | 2013-091625 | 5/2013 |
| KR | 10-2010-0017135 | 2/2010 |
| WO | WO 2012/070309 | 5/2012 |
| WO | WO 2013018827 A1 * | 2/2013 ............... A61K 8/27 |
| WO | WO 2013/031374 | 3/2013 |

OTHER PUBLICATIONS

English Translation of WO2013018827 retrieved from WIPO dated Apr. 28, 2017.*
PCT/JP2015/057832, ISR and Written Opinion, dated Jan. 10, 2015, 2 pages—English, 9 pages—Japanese.
JP 2014-062961, Notice of Reasons for Rejection, dated Jun. 5, 2015, 6 pgs.—English, 6 pgs. —Japanse.
JP 2014-062961, Written Arguments, dated Jul. 30, 2015, 7 pgs.—English, 7 pgs.—Japanese.
JP 2014-062961, Written Amendment, dated Jul. 30, 2015, 1 pg—English, 1 pg.—Japanese.
JP 2014-062961, Decision of Rejection dated Oct. 9, 2015, 5 pgs.13 English, 5 pgs.—Japanese.
JP 2014-062961, Notice of Appeal, dated Jan. 8, 2016, 5 pgs.—English, 5 pgs.—Japanese.
JP 2014-062961, Written Amendment dated Jan. 8, 2016, 1 pg.—English, 1 pg.—Japanese.
JP 2014-062961, Decision to Grant a Patent dated Mar. 4, 2016, 3 pgs.—English, 3 pgs.—Japanese.
JP 2014-062961, Granted Claims in Pub. Grant 2014-062961 (1-page English, 1 page Japanese 1 page Cert. of trans).
Korean Appln. Serial No. 2016-7022398, Office Action dated Oct. 17, 2016, 4 pages—Korean, 4 pages—English.
EP Serial No. 15768574.4, European Search Report, dated Jan. 16, 2017, 7 pages—English.

* cited by examiner

*Primary Examiner* — Jessica Worsham
(74) *Attorney, Agent, or Firm* — Andrew F. Young, Esq.; Lackenbach Siegel, LLP

(57) ABSTRACT

The present application provides an oil-in-water type emulsified cosmetic which has the effect of beautifying the appearance of skin and also excels in emulsion stability. The oil-in-water type emulsified cosmetic according to the present invention is characterized by comprising (A) 1 to 20 mass % of a hydrophobized titanium oxide having an average particle size of at least 0.1 μm; (B) a sugar ester having a carboxyl group within the structure; (C) a liquid higher fatty acid; (D) a higher alcohol; (E) a non-ionic surfactant; (F) water; and (G) an oil component.

4 Claims, No Drawings

OIL-IN-WATER TYPE EMULSIFIED COSMETIC

CROSS REFERENCE TO RELATED APPLICATIONS

This application relates to and claims national phase priority from SN: PCT/JP2015/057832 filed Mar. 17, 2015, the entire contents of which are incorporated herein by reference, which in turn claims priority from JP SN 2014-062961 filed Mar. 26, 2014.

FIGURE SELECTED FOR PUBLICATION

None

BACKGROUND OF THE INVENTION

Field of the Invention

The present invention relates to an oil-in-water type emulsified cosmetic. More specifically, the invention relates to an oil-in-water type emulsified cosmetic which has the effect of beautifying the appearance of skin, while also excelling in emulsion stability.

Description of the Related Art

Titanium oxide is widely used in cosmetics, naturally as white pigments, and due to having a high refractive index, as covering agents for adjusting skin tone such as dullness or redness of the face, concealing color irregularities such as spots and freckles, and improving the appearance of the skin beautifully, and as UV protectants by physically scattering and absorbing UV rays at the particle surface.

When used as covering agents, titanium oxide or titanium oxide agglomerate particles having an average particle size of at least 0.1 μm are generally used. For example, in Patent Document 1, a cosmetic that combines titanium dioxide having an average particle size of 0.1 to 0.5 μm and titanium dioxide of 0.5 to 1.5 μm is described as having a natural skin color and excellent covering ability. Additionally, in Patent Document 2, a cosmetic containing rutile-type titanium dioxide agglomerate particles having a particle size of 0.1 to 5.0 μm is described as excelling in spreadability and sense of finish, excelling in skin coloring ability and concealing ability, and presenting a sense of bare skin without overcoloration.

On the other hand, when used as a UV protectant, fine-particle titanium oxide with an average particle size of less than 0.1 μm, typically 0.05 μm or less, are generally used. For example, Patent Document 3 describes that a cosmetic with abundant UV protection ability, high transparency and no paleness can be obtained by using an ultrafine-particle titanium oxide with an average particle size of 0.005 to 0.05 μm which has been subjected to a specific surface treatment.

In order to blend such particulate powders into a product and achieve lasting effects, the powder must be adequately dispersed in the cosmetic, but powders of small particle size are strongly cohesive, and tend to have inferior dispersibility and emulsion stability. Therefore, in the case of a liquid product, dispersion by mechanical force is not enough, and the emulsion stability must also be improved so that agglomeration does not occur over time.

As a cosmetic with improved stability and dispersibility of fine-particle powders, for example, Patent Document 4 proposes a sunscreen oil-in-water type emulsified cosmetic wherein a powder functioning as a UV scattering agent is subjected to a specific surface treatment, and dispersed using specific oils and dispersion agents.

Additionally, Patent Document 5 indicates that by blending a sunscreen agent, a structuring agent, a hydrophilic surfactant, a thickening agent and water, a gel network structure, liquid crystal structure or both can be formed in the composition, thereby suppressing the destruction of active components and destabilization due to the water in the composition.

However, Patent Documents 4 and 5 both relate to sunscreen cosmetics, and therefore have the purpose of improving the dispersibility of mainly fine-particle powders used as UV scattering agents, i.e. powders generally having an average particle size of less than 0.1 μm, so they are not intended to improve the stability and dispersibility of powders of larger average particle sizes. In general, as the particle size of a powder becomes larger, the cohesive force becomes smaller, and dispersion becomes easier because less dispersion energy is consumed, so there is thought to be a tendency towards improved emulsion stability. However, upon applying these findings described in Patent Documents 4 and 5 to hydrophobized titanium oxide having a skin improvement effect and with larger average particle sizes, the present inventors observed that sufficient emulsion stability was not obtained.

Additionally, while titanium oxide has a higher surface activity than zinc oxides and are considered to be more difficult to disperse than zinc oxides, Patent Document 4 specifically uses zinc oxides as UV scattering agents, and Patent Document 5 does not provide any concrete examples containing titanium oxide as sunscreen agents.

Therefore, an oil-in-water type emulsified cosmetic that stably disperses a hydrophobized titanium oxide having an average particle size of at least 0.1 μm, and that is capable of beautifully improving the appearance of the skin, is sought.

RELATED ART DOCUMENTS

Patent Documents

Patent Document 1: JP 2005-225827 A
Patent Document 2: JP 2008-56535 A
Patent Document 3: JP H8-104613 A
Patent Document 4: JP 2012-111726 A
Patent Document 5: JP H11-504043 A

ASPECTS AND SUMMARY OF THE INVENTION

Problems to be Solved by the Invention

The present invention has the purpose of providing an oil-in-water type emulsified cosmetic having the effect of beautifying the appearance of the skin, while also excelling in emulsion stability and having a refreshing feeling in use.

Means for Solving the Problems

As a result of diligent study into solving the above-mentioned problems, the present inventors discovered that an oil-in-water type emulsified cosmetic excelling in emulsion stability and dispersibility of titanium oxide while also having a refreshing feeling in use can be obtained by blending a combination of a specific sugar ester, a liquid higher fatty acid, a higher alcohol, a non-ionic surfactant, water and an oil component in an oil-in-water type emulsified cosmetic containing a specific amount of a hydrophobized titanium oxide having an average particle size of at least 0.1 μm.

In other words, the present invention provides an oil-in-water type emulsified cosmetic characterized by comprising:

(A) 1 to 20 mass % of a hydrophobized titanium oxide having an average particle size of at least 0.1 μm;

(B) a sugar ester having a carboxyl group within the structure;

(C) a liquid higher fatty acid;

(D) a higher alcohol;

(E) a non-ionic surfactant;

(F) water; and (G) an oil component.

The above and other aspects, features and advantages of the present invention will become apparent from the following description.

BRIEF DESCRIPTION OF THE DRAWINGS

None

DETAILED DESCRIPTION OF THE PREFERRED EMBODIMENTS

Reference will now be made in detail to embodiments of the invention. It will also be understood that other embodiments may be utilized without departing from the scope of the present invention, and that the detailed description is not to be taken in a limiting sense, and that ingredients differently selected may be understood within the scope of the invention as claimed without requirements of the written description being required thereto.

Effects of the Invention

The oil-in-water type emulsified cosmetic of the present invention contains a hydrophobized titanium oxide of at least 0.1 μm having a high refractive index, and therefore presents a natural look of bare skin due to having appropriate levels of coloring ability and concealing ability, and beautifies the appearance of the skin.

Additionally, due to the presence of a sugar ester having a carboxyl group within the structure and a liquid higher fatty acid, the dispersibility of the hydrophobized titanium oxide is improved. Furthermore, due to the formation of an aggregate consisting of a lamellar bimolecular film on the surface of the emulsified particles of the oil-in-water type emulsified cosmetic by the non-ionic surfactant and the higher alcohol in the presence of water, the emulsion stability can be greatly improved. For this reason, it is possible to suppress color streaking that is caused by the hydrophobized titanium oxide dispersed in the inner phase escaping into the outer phase.

Modes for Carrying Out the Invention

Herebelow, the present invention will be described in detail.

(A) Hydrophobized Titanium Oxide

The (A) hydrophobized titanium oxide used in the oil-in-water type emulsified cosmetic of the present invention, in order to increase the concealing ability, contains hydrophobized titanium oxide wherein the average particle size of primary particles is at least 0.1 μm, or a hydrophobized titanium oxide that occurs as lumps of agglomerate particles in the final preparation, wherein the average particle size of the agglomerate particles is at least 0.1 μm. While it is sufficient for the average particle size to be at least 0.1 μm, it should preferably be 0.1 μm to 1 μm, more preferably 0.1 μm to 0.8 μm, and most preferably 0.2 μm to 0.3 μm. If the average particle size is smaller than 0.1 μM, a sufficient skin improvement effect cannot be obtained, and if the size is greater than 1 μm, the scattering is reduced and the improvement effect tends to decrease. On the other hand, hydrophobized titanium oxide with average particle sizes other than those mentioned above may be further included if within a range not compromising the skin improvement effect, dispersibility and emulsion stability of the present invention. The average particle size of the hydrophobized titanium oxide can be measured by observation with a transmission electron microscope (TEM) or the like.

The method for hydrophobization of the titanium oxide is not particularly limited, and a publicly known method may be used. Specific examples include silicone treatments (treatments using silicone oils such as methylhydrogenpolysiloxane, dimethylpolysiloxane and methylphenylpolysiloxane; alkylsilanes such as methyl trimethoxysilane, ethyl trimethoxysilane, hexyl trimethoxysilane, octyl trimethoxysilane and octyl triethoxysilane; or fluoroalkylsilanes such as trifluoromethyl ethyl trimethoxysilane and heptadecafluorodecyl trimethoxysilane), fatty acid treatments (treatments using palmitic acid, isostearic acid, stearic acid, lauric acid, myristic acid, behenic acid, oleic acid, rosin acid and 12-hydroxystearic acid), fatty acid soap treatments (treatments using aluminum stearate, calcium stearate and 12-hydroxystearic acid) and fatty acid ester treatments (treatments using dextrin fatty acid esters, cholesterol fatty acid esters, sucrose fatty acid esters and starch fatty acid esters). Particularly preferred are aluminum stearate treatments and octyl triethoxysilane treatments.

The (A) hydrophobized titanium oxide content should be 1 to 20 mass % with respect to the total amount of the oil-in-water type emulsified cosmetic, preferably 2 to 10 mass %, most preferably 3 to 7 mass %. If the (A) hydrophobized titanium oxide content is less than 1 mass %, a sufficient skin improvement effect cannot be obtained, and if more than 20 mass %, the emulsion stability may be compromised.

(B) Sugar Ester Having a Carboxyl Group within the Structure

The (B) sugar ester having a carboxyl group within the structure used in the oil-in-water type emulsified cosmetic of the present invention, together with the below-described components (C) and (G), constitute the oil phase which is the inner phase of the oil-in-water type emulsified cosmetic. The above-described (A) hydrophobized titanium oxide is evenly dispersed into this oil phase. Examples of the (B) sugar ester having a carboxyl group within the structure include sorbitan sesquiisostearate, dipentaerythrityl fatty acid esters, polyoxyethylene sorbitan monooleate and polyoxyethylene sorbitan monostearate. Sorbitan sesquiisostearate is particularly preferred.

The amount of the (B) sugar ester having a carboxyl group within the structure is preferably 0.1 to 5 mass % with respect to the entire oil-in-water type emulsified cosmetic, more preferably 0.2 to 3 mass %, and most preferably 0.3 to 2 mass %. If the amount of the (B) sugar ester having a carboxyl group within the structure is less than 0.1 mass % or exceeds 5 mass %, the (A) hydrophobized titanium oxide may not be able to be evenly and stably dispersed.

(C) Liquid Higher Fatty Acid

Examples of the (C) liquid higher fatty acid used in the oil-in-water type emulsified cosmetic of the preset invention include isostearic acid, oleic acid, linolic acid and linoleic acid. Isostearic acid is particularly preferred.

The (C) liquid higher fatty acid content is preferably 0.1 to 5 mass % with respect to the entire oil-in-water type emulsified cosmetic, more preferably 0.3 to 3 mass %, and most preferably 0.5 to 2 mass %. If the (C) liquid higher fatty acid content is less than 0.1 mass % or more than 5 mass %, then the (A) hydrophobized titanium oxide may not be able to be evenly and stably dispersed.

(D) Higher Alcohol

The (D) higher alcohol used in the oil-in-water type emulsified cosmetic of the present invention, together with the below-described components (E) and (F), forms an aggregate consisting of a lamellar bimolecular film.

The (D) higher alcohol is not particularly limited as long as it can be used in the fields of cosmetic products, pharmaceutical products and quasi-drugs, and examples include saturated linear monohydric alcohols and unsaturated monohydric alcohols. Examples of saturated linear monohydric alcohols include dodecanol (lauryl alcohol), tridodecanol, tetradodecanol (myristyl alcohol), pentadecanol, hexadecanol (cetyl alcohol), heptadecanol, octadecanol (stearyl alcohol), nonadecanol, icosanol (aralkyl alcohol), henicosanol, docosanol (behenyl alcohol), tricosanol, tetracosanol (carnaubyl alcohol), pentacosanol and hexacosanol (ceryl alcohol). An example of an unsaturated monohydric alcohol is elaidyl alcohol. In the present invention, saturated linear monohydric alcohols are preferred in view of their stability over time.

As the (D) higher alcohol, one or more of the above-described types may be used. In the present invention, a mixture of two or more aliphatic alcohols is preferably used, and a combination such that the melting point of the mixture is at least 60° C. is more preferred. If the melting point is lower than 60° C., the temperature stability of the system can decrease depending on the formulation. In the present invention, for example, a combination of stearyl alcohol and behenyl alcohol is preferred.

The (D) higher alcohol content is preferably 0.1 to 10 mass % with respect to the entire oil-in-water type emulsified cosmetic, and more preferably 0.1 to 5 mass %. If the (D) higher alcohol content is less than 0.1 mass % or more than 10 mass %, sufficient emulsion stability may not be obtained.

(E) Non-Ionic Surfactant

The (E) non-ionic surfactant used in the oil-in-water type emulsified cosmetic of the present invention is not particularly limited, but examples include polyethylene glycol fatty acid esters, polyoxyethylene glyceryl fatty acid esters, polyoxyethylene/methylpolysiloxane copolymers, polyoxyethylene sorbitan fatty acid esters, polyoxyethylene alkyl ethers, maltitol hydroxy aliphatic alkyl ethers, alkylated polysaccharides, alkylglucosides, sucrose fatty acid esters, polyoxyethylene glyceryl hydrogenated castor oil, polyoxyethylene sorbitan fatty acid esters, polyoxyethylene/polyoxypropylene block copolymers, tetrapolyoxyethylene/tetrapolyoxypropylene-ethylene diamine condensates, polyoxyethylene-beeswax/lanolin derivatives, alkanol amides, polyoxyethylene-propylene glycol fatty acid esters, polyoxyethylene-alkylamines, polyoxyethylene-fatty acid amides, alkylethoxydimethylamine oxide and trioleylphosphoric acid, of which those that are hydrophilic are preferred, and those with an HLB of at least 8 are particularly preferred. Particularly preferred examples include beheneth-20, polysorbate 60 and PEG-40 stearate.

One or more types of non-ionic surfactants may be used.

The (E) non-ionic surfactant content is preferably 0.1 to 20 mass % with respect to the entire oil-in-water type emulsified cosmetic, and more preferably 0.3 to 5 mass %. If the (E) non-ionic surfactant content is less than 0.1 mass % or more than 20 mass %, sufficient emulsion stability may not be obtained.

(F) Water

The (F) water that is used in the oil-in-water type emulsified cosmetic of the present invention is not particularly limited, and specific examples include purified water and ion-exchanged water.

The (F) water content should preferably be 25 to 90 mass % with respect to the entire oil-in-water type emulsified cosmetic, more preferably 30 to 80 mass %, and most preferably 30 to 60 mass %. If the (F) water content lies outside the above-indicated range, the stability of the oil-in-water type emulsified cosmetic can decrease, and the refreshing feeling in use may be reduced.

(G) Oil Component

The (G) oil component used in the oil-in-water type emulsified cosmetic of the present invention constitutes an oil phase which is the inner phase of the oil-in-water type emulsified cosmetic. The oil components that can be used in the present invention are not particularly limited, and can be chosen from among those that are used in cosmetic products, within a range that does not compromise stability. Preferred oil components include hydrocarbon oils, polar oils such as ester oils, silicone oils, and liquid oils/fats.

Examples of hydrocarbon oils include liquid paraffin, squalane, squalene, paraffin, isoparaffin, ceresin, isohexadecane and isododecane.

Examples of polar oils such as ester oils include pentaerythrityl tetraethylhexanoate, cetyl ethylhexanoate, jojoba oil, di(phytosteryl/octyldodecyl) lauroylgiutamate, triisostearin, glyceryl diisostearate, triethylhexanoin, (phytosteryl/behenyl) dimer dilinoleate, (phytosteryl/isostearyl/cetyl/stearyl/isostearyl/cetyl/stearyl/behenyl) dimer dilinoleate, isopropyl palmitate, phytosteryl macadamiate, pentaerythrityl tetra(behenate/benzoate/ethylhexanoate), ethylhexyl palmitate, myristyl myristate, isopropyl myristate, tripropylene glycol dipivalate, diisopropyl sebacate and isodecyl neopentanoate.

Examples of silicone oils include chain-type silicones such as dimethylpolysiloxane, methylphenylpolysiloxane and methylhydrogenpolysiloxane, cyclic silicones such as octamethylcyclotetrasiloxane, decamethylcyclopentasiloxane and dodecamethylcyclohexasiloxane, silicone resins forming three-dimensional mesh structures, and silicone rubber.

Examples of liquid oils/fats include amani oil, Japanese camellia oil, macadamia nut oil, corn oil, mink oil, olive oil, avocado oil, sasanqua oil, castor oil, safflower oil, rapeseed oil, soybean oil, peanut oil, triglycerin, glycerin trioctanoate and glycerin triisopalmitate.

Additionally, UV absorbing agents can be used as the oil component in the present invention. Examples of UV absorbing agents include octylmethoxycinnamate, octocrylene, polysilicone-15, bis-resorcinyltriazine, ethylhexyltriazone, diethylamino hydroxybenzoyl hexyl benzoate and oxybenzone-3.

The (G) oil component content is not particularly limited, but is preferably 5 to 30 mass % with respect to the entire oil-in-water type emulsified cosmetic.

The oil-in-water type emulsified cosmetic of the present invention may, in addition to the above-mentioned essential components, appropriately contain components that are normally blended into cosmetics, such as humectants, thickening agents, powders, alcohols, natural polymers, synthetic polymers, sugars, antioxidants, buffers, various extracts, stabilizing agents, preservatives, pigments and fragrances, within a range not compromising the effects of the present invention.

The oil-in-water type emulsified cosmetic of the present invention may, for example, be produced by using an HM mixer or the like to mix and stir a powder containing the (A) hydrophobized titanium oxide into a mixture of the (B) sugar ester having a carboxyl group within the structure, (C) liquid higher fatty acid, and a portion of the (G) oil component to prepare a dispersion part; dissolving the remaining (G) oil component, (D) higher alcohol and (E) non-ionic surfactant at a high temperature to prepare a dissolved oil part; and finally adding the dispersion part and the dissolved oil part to a heated water phase part containing the (F) water and other aqueous components, and emulsifying by conventional methods and cooling.

The oil-in-water type emulsified cosmetic obtained by this production method excels in emulsion stability, so that there is no color streaking caused by the hydrophobized titanium oxide dispersed in the inner phase escaping into the outer phase during use, and there is an effect of beautifying the appearance of the skin while having a refreshing feeling in use.

EXAMPLES

Herebelow, the present invention will be explained in further detail with reference to examples, but the present invention is not limited thereby. Where not otherwise indicated, amounts are given in mass % with respect to the entire amount.

Oil-in-water type emulsified cosmetics with the formulations shown in Table 1 and Table 2 were produced by the below-described production method and evaluated as follows.

<Production Method>
[Preparation of Dispersion Part]
(19) to (25) were added to a mixture of (15) to (18), and the result was mixed and stirred using an HM mixer or the like.
[Preparation of Dissolved Oil Part]
(9) to (14) were dissolved and mixed at 70° C.
[Preparation of Water Phase Part]
(2) to (8) were added to (1) and dissolved.
[Preparation of Oil-in-Water Type Emulsified Cosmetic]
The above-mentioned water phase part was heated to 70° C. the dispersion part and dissolved oil part were added, emulsified by a conventional method, and cooled to obtain an oil-in-water type emulsified cosmetic.
<Evaluation Method>
[Effect of Beautifying the Appearance of Skin]
The cosmetics of the examples and the comparative examples were applied to the entire face, the effect of beautifully improving the appearance of the skin was observed by eye, and judged according to the following criteria.
<Evaluation Criteria>
A: clear improvement effects were observed
B: some improvement effects were observed
C: improvement effects were mostly not observed
D: absolutely no improvement effects were observed
[Emulsion Stability in Oil-in-Water Type Emulsified Cosmetic]
Whether or not color streaking or the like caused by powder escaping from the inner phase occurred at the wall surfaces of the container (tube) when using the cosmetics of the examples and the comparative examples was observed by eye, and judged by the following evaluation criteria.
<Evaluation Criteria>
A: absolutely no color streaking observed
B: slight color streaking observed but within a tolerable range
C: color streaking beyond the tolerable range observed
D: color streaking clearly observed

TABLE 1

|  | Comp. Ex. 1 | Comp. Ex. 2 | Comp. Ex. 3 | Comp. Ex. 4 | Comp. Ex. 5 |
| --- | --- | --- | --- | --- | --- |
| (1) Water | bal | bal | bal | bal | bal |
| (2) Alcohol | 6 | 6 | 6 | 6 | 6 |
| (3) Glycerin | 5 | 5 | 5 | 5 | 5 |
| (4) Edetic acid | 0.1 | 0.1 | 0.1 | 0.1 | 0.1 |
| (5) PEG-60 hydrogenated castor oil | 3 | 3 | 3 | 3 | 3 |
| (6) Succinoglycan | 0.1 | 0.1 | 0.1 | 0.1 | 0.1 |
| (7) (Dimethylacrylamide/sodium acryloyl dimethyl taurate) cross-polymer | 0.5 | 0.5 | 0.5 | 0.5 | 0.5 |
| (8) Cellulose gum | 0.2 | 0.2 | 0.2 | 0.2 | 0.2 |
| (9) Octylmethoxycinnamate | 10 | 10 | 10 | 10 | 10 |
| (10) Bis-ethylhexyloxyphenol methoxyphenyl triazine | 3 | 3 | 3 | 3 | 3 |
| (11) Diethylamino hydroxybenzoyl hexyl benzoate | 3 | 3 | 3 | 3 | 3 |
| (12) Beheneth-20 | — | — | — | — | 1 |
| (13) Behenyl alcohol | — | — | — | — | 0.7 |
| (14) Stearyl alcohol | — | — | — | — | 0.2 |
| (15) Isododecane | 10 | 10 | 10 | 10 | 10 |
| (16) Caprylyl methicone | 5 | 5 | 5 | 5 | 5 |
| (17) Isostearic acid | 1 | 1 | 1 | 1 | 1 |
| (18) Sorbitan sesquiisostearate | 0.5 | 0.5 | 0.5 | 0.5 | 0.5 |
| (19) Hydrophobized zinc oxide | 10 | 10 | 10 | 10 | 10 |
| (20) Hydrophobized fine particle titanium oxide (average particle size 0.03 to 0.09 μm) | 5 | — | — | — | 5 |
| (21) Hydrophobized titanium oxide (average particle size 0.1 μm) | — | 5 | — | — | — |

TABLE 1-continued

|  | Comp. Ex. 1 | Comp. Ex. 2 | Comp. Ex. 3 | Comp. Ex. 4 | Comp. Ex. 5 |
|---|---|---|---|---|---|
| (22) Hydrophobized titanium oxide (average particle size of agglomerate particles 0.11 to 0.15 μm) | — | — | 5 | — | — |
| (23) Hydrophobized titanium oxide (average particle size 0.2 to 0.3 μm) | — | — | — | 5 | — |
| (24) Hydrophobized iron oxide (red) | 0.2 | 0.2 | 0.2 | 0.2 | 0.2 |
| (25) Hydrophobized iron oxide (yellow) | 0.05 | 0.05 | 0.05 | 0.05 | 0.05 |
| Evaluation Effect of beautifying appearance of skin | C | A | A | A | C |
| Emulsion stability in oil-in-water type emulsified cosmetic | B | D | D | D | A |

TABLE 2

|  | Ex. 1 | Ex. 2 | Ex. 3 | Ex. 4 | Ex. 5 |
|---|---|---|---|---|---|
| (1) Water | bal | bal | bal | bal | bal |
| (2) Alcohol | 6 | 6 | 6 | 6 | 6 |
| (3) Glycerin | 5 | 5 | 5 | 5 | 5 |
| (4) Edetic acid | 0.1 | 0.1 | 0.1 | 0.1 | 0.1 |
| (5) PEG-60 hydrogenated castor oil | 3 | 3 | 3 | 3 | 3 |
| (6) Succinoglycan | 0.1 | 0.1 | 0.1 | 0.1 | 0.1 |
| (7) (Dimethylacrylamide/sodium acryloyl dimethyl taurate) cross-polymer | 0.5 | 0.5 | 0.5 | 0.5 | 0.5 |
| (8) Cellulose gum | 0.2 | 0.2 | 0.2 | 0.2 | 0.2 |
| (9) Octylmethoxycinnamate | 10 | 10 | 10 | 10 | 10 |
| (10) Bis-ethylhexyloxyphenol methoxyphenyl triazine | 3 | 3 | 3 | 3 | 3 |
| (11) Diethylamino hydroxybenzoyl hexyl benzoate | 3 | 3 | 3 | 3 | 3 |
| (12) Beheneth-20 | 1 | 1 | 1 | 1 | 1 |
| (13) Behenyl alcohol | 0.7 | 0.7 | 0.7 | 0.7 | 0.7 |
| (14) Stearyl alcohol | 0.2 | 0.2 | 0.2 | 0.2 | 0.2 |
| (15) Isododecane | 10 | 10 | 10 | 10 | 10 |
| (16) Caprylyl methicone | 5 | 5 | 5 | 5 | 5 |
| (17) Isostearic acid | 1 | 1 | 1 | 1 | 1 |
| (18) Sorbitan sesquiisostearate | 0.5 | 0.5 | 0.5 | 0.5 | 0.5 |
| (19) Hydrophobized zinc oxide | 10 | 10 | 10 | 10 | 10 |
| (20) Hydrophobized fine particle titanium oxide (average particle size 0.03 to 0.09 μm) | — | — | — | — | — |
| (21) Hydrophobized titanium oxide (average particle size 0.1 μm) | 5 | — | — | 15 | — |
| (22) Hydrophobized titanium oxide (average particle size of agglomerate particles 0.11 to 0.15 μm) | — | 5 | — | — | 10 |
| (23) Hydrophobized titanium oxide (average particle size 0.2 to 0.3 μm) | — | — | 5 | — | — |
| (24) Hydrophobized iron oxide (red) | 0.2 | 0.2 | 0.2 | 0.2 | 0.2 |
| (25) Hydrophobized iron oxide (yellow) | 0.05 | 0.05 | 0.05 | 0.05 | 0.05 |
| Evaluation Effect of beautifying appearance of skin | A | A | A | A | A |
| Emulsion stability in oil-in-water type emulsified cosmetic | A | A | A | B | B |

As shown in Table 1, when components (D) and (E) of the present invention were not included, excellent emulsion stability was achieved when using hydrophobized fine particle titanium oxide with particle sizes smaller than component (A), but the skin improvement effect was insufficient (Comparative Example 1). Additionally, when using a hydrophobized titanium oxide satisfying the average particle size of component (A), sufficient emulsion stability was not able to be obtained (Comparative Examples 2 to 4). On the other hand, even if components (D) and (E) of the present invention were included, when using hydrophobized fine particle titanium oxide having a smaller particle size than component (A) of the present invention, excellent emulsion stability was achieved, but sufficient skin improvement effects could not be achieved (Comparative Example 5).

On the other hand, as shown in Table 2, the oil-in-water type emulsified cosmetic containing all the essential components of the present invention achieved excellent effects for both skin improvement and emulsion stability (Examples 1-5).

Formulation Examples

Herebelow, formulation examples of the oil-in-water type emulsified cosmetic of the present invention will be provided. The fact that the present invention is not in any way limited by these formulation examples and is not specified by the claims should go without saying. The amounts are all given in mass % with respect to the entire amount of the product.

Formulation Example 1

| (Component name) | Amount (mass %) |
|---|---|
| (1) Water | balance |
| (2) Edetic acid | 0.1 |
| (3) PEG-100 hydrogenated castor oil | 2 |
| (4) Xanthan gum | 0.1 |
| (5) (PEG-240/decyltetradeceth-20/HDI) copolymer | 0.5 |
| (6) Diisopropyl sebacate | 10 |
| (7) Bis-ethylhexyloxyphenol methoxyphenyl triazine | 1 |
| (8) Diethylamino hydroxybenzoyl hexyl benzoate | 1 |
| (9) Polysorbate 60 | 1.2 |
| (10) Behenyl alcohol | 0.7 |
| (11) Stearyl alcohol | 0.2 |
| (12) Cyclomethicone | 15 |
| (13) Isostearic acid | 1 |
| (14) Sorbitan sesquiisostearate | 0.5 |
| (15) Hydrophobized zinc oxide | 10 |
| (16) Hydrophobized titanium oxide (average particle size 0.1 μm) | 5 |
| (17) Hydrophobized iron oxide (red) | 0.2 |
| (18) Hydrophobized iron oxide (yellow) | 0.05 |

Formulation Example 2

| (Component name) | Amount (mass %) |
|---|---|
| (1) Water | balance |
| (2) Edetic acid | 0.1 |
| (3) PEG-100 hydrogenated castor oil | 3 |

-continued

| (Component name) | Amount (mass %) |
|---|---|
| (4) Octylmethoxycinnamate | 8 |
| (5) PEG-40 stearate | 0.7 |
| (6) Behenyl alcohol | 0.7 |
| (7) Stearyl alcohol | 0.2 |
| (8) Isohexadecane | 8 |
| (9) Caprylyl methicone | 5 |
| (10) Isostearic acid | 1 |
| (11) Sorbitan sesquiisostearate | 0.5 |
| (12) Hydrophobized titanium oxide (average particle size 0.1 μm) | 12 |
| (13) Hydrophobized iron oxide (red) | 0.2 |
| (14) Hydrophobized iron oxide (yellow) | 0.05 |

Formulation Example 3

| (Component name) | Amount (mass %) |
|---|---|
| (1) Water | balance |
| (2) Edetic acid | 0.1 |
| (3) PEG-100 hydrogenated castor oil | 3 |
| (4) Succinoglycan | 0.1 |
| (5) (Sodium acrylate/sodium acryloyl dimethyltaurate) copolymer | 1 |
| (6) Di-(2-ethylhexyl)-4'-methoxybenzalmalonate | 10 |
| (7) Ethylhexyl triazine | 1 |
| (8) Oxybenzone-5 | 1 |
| (9) Polysorbate 60 | 0.7 |
| (10) Behenyl alcohol | 0.7 |
| (11) Stearyl alcohol | 0.2 |
| (12) Cyclomethicone | 8 |
| (13) Isohexadecane | 5 |
| (14) Isostearic acid | 1 |
| (15) Sorbitan sesquiisostearate | 0.5 |
| (16) Hydrophobized fine particle titanium oxide (average particle size 0.03 to 0.09 μm) | 3 |
| (17) Hydrophobized titanium oxide (average particle size 0.2 to 0.3 μm) | 7 |
| (18) Hydrophobized iron oxide (red) | 0.2 |
| (19) Hydrophobized iron oxide (yellow) | 0.05 |

Having described at least one of the preferred embodiments of the present invention, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:
1. An oil-in-water emulsified cosmetic, comprising:
   (A) 1 to 20 mass % of a hydrophobized titanium oxide having an average particle size between 0.2 μm and 1 μm;
   (B) a sugar ester selected from the group consisting of sorbitan sesquiisostearate, dipentaerythrityl fatty acid esters, polyoxyethylene sorbitan monooleate and polyoxyethylene sorbitan monostearate;
   (C) a liquid higher fatty acid;
   (D) a higher alcohol;
   (E) a non-ionic surfactant which is not the sugar ester;
   (F) water; and
   (G) an oil component,
   wherein the titanium oxide is dispersed in the oil phase.
2. The oil-in-water emulsified cosmetic according to claim 1, wherein:
   the (D) higher alcohol is a combination of stearyl alcohol and behenyl alcohol.
3. The oil-in-water emulsified cosmetic according to claim 1, wherein:
   the (E) non-ionic surfactant is one or two selected from the group consisting of beheneth-20 and PEG-40 stearate.
4. The oil-in-water emulsified cosmetic according to claim 2, wherein:
   the (E) non-ionic surfactant is one or two selected from the group consisting of beheneth-20 and PEG-40 stearate.

\* \* \* \* \*